(12) United States Patent
Larsen et al.

(10) Patent No.: US 7,084,122 B2
(45) Date of Patent: Aug. 1, 2006

(54) USE OF GLYCOSIDES OF MONO- AND DIACYGLYCEROL AS ANTI-INFLAMMATORY AGENTS

(76) Inventors: Erik Larsen, Övad 7838, 26492, Klippan (SE); Arsalan Kharazmi, Bernstorffsvej 9, DK-2900, Hellerup (DK); Søren Brøgger Christensen, Åtoften 187, DK-2990, Nivå (DK); Lars Porskjær Christensen, Bøgeparken 18, Sdr. Nærå DK-5792, Årslev (DK); Kirsten Brandt, Knud Bankesgyden 22, DK-5792, Arslev (DK)

( * ) Notice: Subject to any disclaimer, the term of this patent is extended or adjusted under 35 U.S.C. 154(b) by 10 days.

(21) Appl. No.: 10/300,831

(22) Filed: Nov. 21, 2002

(65) Prior Publication Data
US 2003/0139350 A1  Jul. 24, 2003

Related U.S. Application Data

(60) Provisional application No. 60/358,391, filed on Feb. 22, 2002, provisional application No. 60/332,084, filed on Nov. 21, 2001, provisional application No. 60/341,609, filed on Dec. 18, 2001.

(51) Int. Cl.
A61K 31/70 (2006.01)

(52) U.S. Cl. ..................................................... 514/25
(58) Field of Classification Search ................ 575/25; 536/4.1; 514/25, 887
See application file for complete search history.

(56) References Cited

U.S. PATENT DOCUMENTS

| | | | |
|---|---|---|---|
| 5,486,536 A | 1/1996 | Ward et al. | |
| 5,620,962 A | 4/1997 | Winget | |
| 5,767,095 A | 6/1998 | Winget | |
| 6,024,960 A | * 2/2000 | Kharazmi et al. | .......... 424/765 |

FOREIGN PATENT DOCUMENTS

| | | |
|---|---|---|
| DE | 19634019 A1 | 2/1998 |
| DE | 19634021 A1 | 2/1998 |
| EP | 0671406 A2 | 9/1995 |
| EP | 0671407 A2 | 9/1995 |
| EP | 0671407 A3 | 9/1995 |
| JP | 05-271270 | 10/1993 |
| JP | 06-336437 | 12/1994 |
| JP | 07-149786 | 6/1995 |
| WO | 94/24984 | 11/1994 |
| WO | 98/30573 | 7/1998 |

OTHER PUBLICATIONS

English language translation of DE 196 34 019, published Feb. 26, 1998.*
Nagatsu, Akito et al., "Synthesis and Structure—Anti-Tumor-Promoting Activity relationship of Mongalactosyl Diacylglycerols", *Bioorganic & Medicinal Chemistry* (1994), vol. 4, No. 13, pp. 1619-1622.
Erdem Yesilada et al., "Inhibitory effects of Turkish folk remedies on inflammatory cytokines: interleukin-$1\alpha$, interleukin-$1\beta$ and tumor necrosis factor $\alpha$," Journal of Ethnopharmacology 58, (1997), 59-73.
Tiwalade A. Olugbade et al., "Prieurianoside, a protolimonoid glucoside from the leaves of *Trichilia prieuriana*," Phytochemistry 54, (2000) 867-870.
International Search Report for Application No. PCT/DK02/00783, dated Apr. 23, 2003.
Naoki Ohta et al., "Synthesis of biologically active galactosyl and glucosyl-glycerol derivatives," Chem. Pharm. Bull. 39(5) 1337-1339 (1991).
Hirotaka Shibuya et al., "Syntheses of a Glycerophospholipid, C16-Platelet Activating Factor and a Palmitoyl Analogue of M-5 an Anti-inflammatory Glyceroglycolipid[1]." Chem. Pharm. Bull. 40(5) 1166-1169 (1992).
Cateni, F[1] et al., Biologically active compounds from Euphorbiaceae; Three new glycolipids with anti-inflammatory activity from *Euphobia cyparissias* L., Pharm. Pharmacol Lett (2001) 2: 53-57.

(Continued)

Primary Examiner—Elli Peselev
(74) Attorney, Agent, or Firm—Hunton & Williams

(57) ABSTRACT

Glycosides of diacylglycerol, e.g. 3-$\beta$-D-galactopyranosyloxy-2-(octadeca-9Z,12Z,15Z-trienoyloxy)propanyl octadeca-9Z,12Z,15Z-trienoate (GOPO), which was isolated from extracts of rose-hips by activity guided fractionation, can be used as an oral anti-inflammatory agent for the treatment of inflammatory diseases such as arthritis and osteoarthrosis.

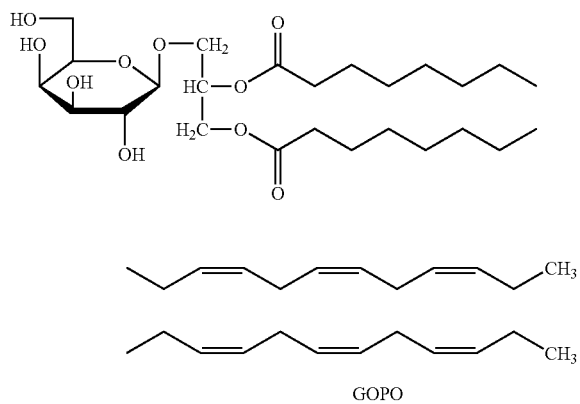

GOPO

21 Claims, 2 Drawing Sheets

OTHER PUBLICATIONS

Chul Kim et al., "Galactolipids from mori folium and their hypoglycemic effect," Saengyak Hakhoechi (2000), 31(1), 95-100, ABSTRACT.

Nobutoshi Murakami et al., "An autolytic substance in a freshwater cyanobacterium phormidium tenue," Chem. Pharm. Bull. 38(3), pp. 812-814 (1990).

Nobutoshi Murakami et al., "Seven new monogalactosyl diacylglycerols isolated from the axenic cyanobacterium phormidium tenue[1]," Chem. Pharm. Bull. 38(2), pp. 3497-3499, (1990).

Takashi Morimoto et al., "Anti-tumor-promoting glyceroglycolipids from the green alga, chlorella vlgaris," Phytochemistry vol. 40, No. 5, pp. 1433-1437, (1995).

Hideaki Shirahashi et al., "Isolation and identification of anti-tumor-promoting principles from the fresh water cyanobacterium phomidium tenue[1]," Chem. Pharm. Bull. 41(9), pp. 1664-1666 (1993).

J. Jakupovic et al., Millerenolides, sesquiterpene lactones from millenia quinqueflora, Phytochemistry, vol. 26, No. 7, pp. 2011-2017, 1987.

Putul Baruah et al., "A monoacyl galactosylglycerol from sonchus arvensis," Phytochemistry, vol. 22, No. 8, pp. 1741-1744, 1983.

Akira Murakami et al., "Glyceroglycolipids from citrus hystrix, a traditional herb in Thailand, potently inhibit the tumor-promoting activity of 12-O-Tetradecanoylphorbol 13-Acetate in mouse skin," J. Agric. Food Chem. 1995, 43, pp. 2779-2783.

K. Winther et al., "The anti-inflammatory properties of rose-hip," Inflammopharmacology, vol. 7, No. 1, pp. 63-68, (1999).

Hirotaka Shibuya et al., "Syntheses of a glycerophospholipid, c16-platelet activating factor and a palmitoyl analogue of an anti-inflammatory glyceroglycolopid[1]," Chem. Pharm. Bull. 40(5), pp. 1166-1169 (1992.

Naoki Ohta et al., "Synthesis of biologically active galactosyl and glucosyl-glycerol derivatives," Chem. Pharm. Bull. 39(5), pp. 1337-1339 (1991.

Hiroyuki Kikuchi et al., "Foliaspongin, an antiinflammatory bishomosesterterpene from the marine sponge phyllospongia foliascens (Pallas)." Chem. Pharm. Bull. 29(5), pp. 1492-1494 (1981).

Hiroyuki Kikuchi et al., "Marine natural products. X[1]. Pharmacologically active glycolipids from the Okinawan Marine sponge phyllospongia foliascens (Pallas)," Chem. Pharm. Bull. 30(10), pp. 3544-3547 (1982).

Armandodoriano Bianco et al., "Microcomponents of olive oil. Part II: Digalactosyldiacylglycerols from Olea europea," Food Chemistry, vol. 62, No. 3, pp. 343-346, (1998).

Jee H. Jung et al., "Diacylglycerylgalactosides from arisaema amurense," Phytochemistry, vol. 42, No. 2, pp. 447-452, 1996.

Ryo Yamauchi et al., "Analysis of molecular species of glycolipids in fruit pastes of red bell pepper (capsicum annuum L.) by high-performance liquid chromatography-mass spectrometry," J. Agric. Food Chem. (2001), 49, pp. 622-627.

Rene Suhr et al., "Synthesis of glycosyl glycerols and related glycolipids," J. Carbohydrate Chemistry, 17(6), pp. 937-968 (1998).

X.-M. Wang et al., "Comparison of fatty acid composition in tissues of low linolenate mutants of soybean," Phytochemistry, vol. 28, No. 2, pp. 411-414, (1989).

Isao Kitagawa et al., Saponin and Sapogenol. XLVI.[1] On the constituents in aerial part of American Alfalfa, Medicago sativa L. The structure of dehydrosoyasaponin I, Yakugaku Zasshi, 108(6), pp. 547-554 (1988).

Nobutoshi Murakami et al., "Studies on glycolipids. III.[1] Glyceroglycolipids from an axenically cultured cyanobacterium phormidium tenue," Chem. Pharm. Bull. 39(9), pp. 2277-2281 (1991).

Christian Wegner et al., "Tensioactive compounds from the aquatic plant ranunculus fluitans L. (Ranunculaceae)," Helvetica Chimica Acta, vol. 83, pp. 1454-1464, (2000).

Naoki Ohta et al., "Synthesis of biologically active galactosyl and glucosy-glycerol derivates," Chem. Pharm. Bull. 39(5), pp. 1337-1339, (1991).

Arsalan Kharazmi et al., "Rose hip inhibits chemotaxis and chemiluminescence of human peripheral blood neutrophils in vitro and reduces certain inflammatory parameters in vivo," Inflammopharmocology, vol. 7, No. 4, pp. 377-386 (1999).

Peter Libby, "Atherosclerosis: The new view," Scientific American, May 2002, pp. 29-37.

T. Ringbom, et al., "COX-2 Inhibitory effects of naturally occuring and modified fatty acids," J. Nat. Prod. 2001, 64, pp. 745-749.

Hiroyuki Kikuchi et al., "Marine natural products. XI.[1] Antiinflammatory scalarane-type bishomosestertterpene foliaspongin, from the Okinawan Marine sponge phyllospongia foliascens (Pallas)," Chem. Pharm. Bull. 31(2), pp. 552-556 (1983).

\* cited by examiner

USE OF GLYCOSIDES OF MONO- AND DIACYGLYCEROL AS ANTI-INFLAMMATORY AGENTS

CROSS-REFERENCE TO RELATED APPLICATIONS

We claim priority from the following U.S. patent applications: 60/332,084 filed Nov. 21, 2001, 60/341,609, filed Dec. 18, 2001 and 60/358,391, filed Feb. 22, 2002.

FIELD OF THE INVENTION

This invention relates to the use of glycosides of mono- or diacylglycerol, e.g. 3-β-D-galactopyranosyloxy-2-(octadeca-9Z,12Z,15Z-trienoyloxy)propanyl octadeca-9Z,12Z, 15Z-trienoate (a constituent of rose-hips (the fruits of *Rosa canina* L.)), for the treatment of inflammatory conditions, e.g. treatment of inflammation by alleviating chemotaxis and oxidative burst response of leukocytes.

BACKGROUND OF THE INVENTION

The anti-inflammatory properties of water-extracts of rose-hips have previously been reported (Winther, Rein, and Kharazmi, Inflammopharmacology, Vol. 7, pp 63–68 (1999)). Extracts of rose-hips are also known to inhibit chemotaxis and chemiluminescence of human peripheral blood neutrophils in vitro and to reduce certain inflammatory parameters in vivo (Kharazmi and Winther, Inflammopharmacology, Vol.7, pp 377–386 (1999)).

In U.S. Pat. No. 6,024,960, a rose-hip concentrate having a high content of vitamin C was found to alleviate the symptoms associated with inflammation. Specifically, the concentrate was obtained in accordance with a process that preserved a relatively high vitamin C content as well as the content of a number of other vitamins. In the applicants' related U.S. patent application Ser. No. 09/694,764, filed on Oct. 23, 2000, the oral administration of a combination of a rose-hip concentrate and fish oil is described as being useful in the alleviation of joint pain and stiffness, particularly in relation to arthritis. However, the quantity of rose-hip concentrate described in each of these applications as being useful to obtain a beneficial effect was relatively high and somewhat inconvenient for daily usage.

In U.S. Pat. Nos. 5,620,962 and 5,767,095, monogalactosyl dieicosapentaenoyl glycerol (MGDG-EPA) obtained from marine algae was described as having anti-inflammatory properties when used in a topical formulation. These patents describe that only galactosyl glycerols esterified with at least one eicosapentaenoic acids moiety possess topical anti-inflammatory properties.

β-D-Galactopyranosylglycerols esterified with a 1:10:10 mixture of myristic, palmitic and palmotoleic acid were claimed modestly to inhibit superoxide radical formation (Kikuchl, H., Tsukitani, Y., Shimizu, I., Kobayashi, M., Kitagawa, I: Chem. Pharm. Bull. Vol. 31 pp 552–556 (1983)), but no further investigations of the anti-inflammatory properties of this mixture of compounds and of the potential medical uses have been performed.

SUMMARY OF THE INVENTION

In the applicants' continuing studies of concentrates of rose-hips, the applicants have surprisingly discovered that a particular constituent of rose-hips is a highly active anti-inflammatory agent. Since rose-hips taken orally efficiently alleviate inflammatory pains such as the pain associated with arthritis, a formulation of the identified anti-inflammatory agent is believed to be useful for the treatment of symptoms associated with inflammatory diseases. The isolated substance was identified as the galactolipid 3-β-D-galactopyranosyl-oxy-2-(octadeca-9Z, 12Z,15Z-trienoyloxy)propanyl octadeca-9Z,12Z, 15Z-trienoate (1,2-di-O-α-linolenoyl-3-O-β-D-galactopyranosyl-glycerol), as will be described further below. Surprisingly, this compound was found to potently inhibit chemotaxis as well as chemiluminescence of polymorphonuclear leukocytes.

It is thus an object of the present invention to provide a method for the treatment, alleviation or prevention of inflammatory conditions by utilising a medicament comprising glycosides of mono- or diesters of glycerol with the exception of esters of eicosapentaenoic acid, and especially of 3-β-D-galactopyranosyloxy-2-(octadeca-9Z,12Z,15Z-trienoyloxy)propanyl octadeca-9Z,12Z,15Z-trienoate (in short, "GOPO") or related compounds. In a particular aspect of the invention, the medicament is adapted for oral use and for alleviating the symptoms of inflammatory diseases, such as arthritis and osteoarthrosis (i.e. diseases causing joint pains or joint stiffness) including relief of pain, reduction of inflammation and increase of motion.

This and other objects of the present invention are achieved by glycosides of mono- or diesters (or ethers) of glycerol with the exception of esters of eicosapentaenoic acid, in particular as defined in claim 1.

DETAILED DESCRIPTION OF THE INVENTION

Figure 1:
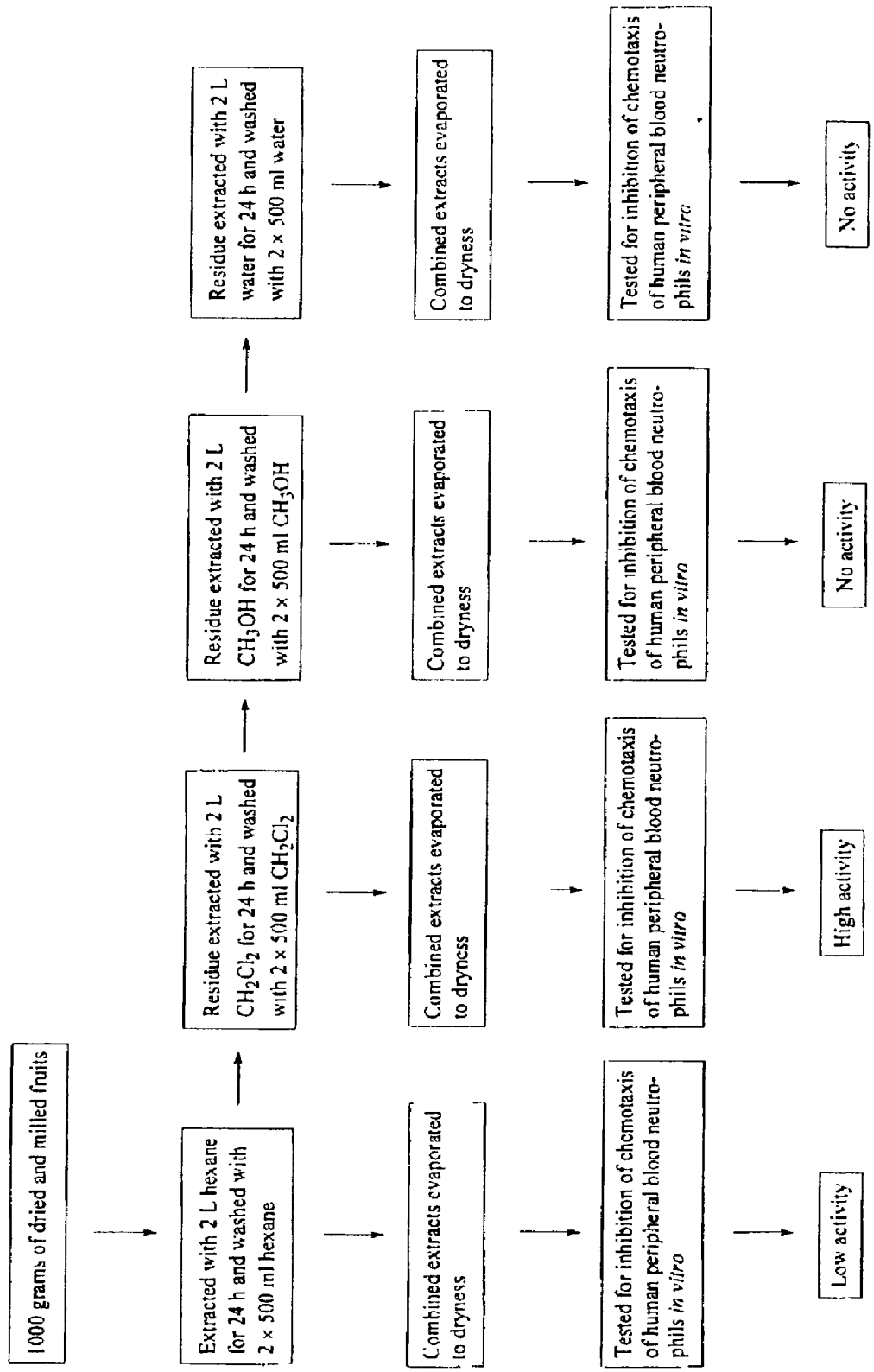
FIG. 1 illustrates the first step of the fractionation process originally used in order to isolate the anti-inflammatory agent from rose-hips of *Rosa canina* L.

The terms "glycoside of a mono- or diesterified glycerol", "glycosides of mono- or diacylglycerol" and similar terms are intended to mean a class of glycosides of mono- or diacylglycerols (as well as ethers), such as those which can be isolated from plants as illustrated by the various formulas herein, and which are not esters of eicosapentaenoic acid. The "glycoside" part is typically a pentose, hexose or heptose, in particular hexoses such as galactose and glucose, e.g. galactose, but can also be di- and oligosaccharides containing two or more sugar moieties in combination, in particular diglycosides such as digalactosides and diglucosides, e.g. 6-O-(α-D-galactopyranosyl)-β-D-galactopyranose.

Thus, the present invention provides the use of a compound of the formula I:

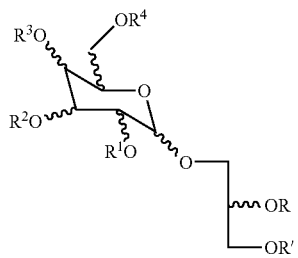

wherein R and R' independently are selected from hydrogen, $C_{10-24}$-alkyl, and $C_{10-24}$-acyl, said alkyl and acyl groups having 0 to 5 unsaturated bonds, and $R^1$, $R^2$, $R^3$ and $R^4$ independently are selected from hydrogen and glycoside moieties; with the first proviso that not both of R and R' are hydrogen, and with the second proviso that none of R and R' is eicosapentaenoyl, for the preparation of a medicament for the treatment, alleviation or prophylaxis of inflammatory conditions in a mammal.

The "wavy bonds" in the formulae presented herein are intended to mean that the carbon on which the substituent in question is positioned may be in the (R) or (S) configuration. In the "sugar" moiety (glycoside) the two different configurations are some times designated α and β. A particular interesting combination is glucose or galactose in the β-pyranose form.

Although the "sugar" moiety in the formulae presented herein is drawn in the pyranose form, it will be understood that the anti-inflammatory agent may also be present in the furanose form (or a mixture of the pyranose and furanose forms) as a solid and in solution.

In the present context, the term "$C_{10-24}$-alkyl" is intended to mean a linear or branched hydrocarbon group having 10 to 24 carbon atoms, e.g., decyl, undecyl, dodecyl, tetradecyl, hexadecyl, octadecyl, nonadecyl, eicodecyl, etc.

In the present context, the term "$C_{10-24}$-acyl" is intended to mean a linear or branched hydrocarbon group having 10 to 24 carbon atoms wherein the first carbon of the group is a carbonyl ($C_{9-23}$-alkyl-C(=O)—), i.e. a fatty acid residue having 10 to 24 carbon atoms. Examples hereof are the residues of lauric acid (C12), myristic acid (C14), palmitic acid (C16), stearic acid (C18), etc.

The alkyl and acyl groups may have 0 to 5 unsaturated bonds such as double or triple bonds, in particular double bonds. Examples of acyl groups having one or more unsaturated double bonds are the residues of palitoleic acid (C16:1), oleic acid (C18:1), linoleic acid (C18:2), linolenic acid (C18:3), arachidonic acid (C20:3), retinoic acid (C20:5), etc.

More specifically, the glycosides of mono- or diesters (or ethers) of glycerol are diesters, diethers, or monoether-monoesters, i.e. R and R' are independently selected from $C_{10-24}$-alkyl and $C_{10-24}$-acyl. The currently most preferred are glycosides of diesters, i.e. R and R' are independently $C_{10-24}$-acyl. In all instances, the alkyl and acyl groups have 0 to 5 unsaturated bonds.

With respect to the degree of saturation of the alkyl and acyl groups, it is currently believed that any alkyl and acyl groups having 0 to 4 unsaturated bonds, such as 1–3 unsaturated bonds, e.g. 2 or 3 unsaturated bonds, in particular 3 unsaturated bonds, are the most suitable as R and R'.

Also, it is currently believed that any unsaturated bonds preferably are double bonds.

This being said, it is envisaged that particularly interesting anti-inflammatory agents are those where R and R' both are $C_{16-20}$-acyl having 1 to 3 double bonds, such as $C_{18}$-acyl having 3 double bonds, in particular where the "sugar" moiety is glucose or galactose, in particular galactose.

As mentioned above, $R^1$, $R^2$, $R^3$ and $R^4$ are independently selected from hydrogen and glycoside moieties, preferably only at the most one of $R^1$, $R^2$, $R^3$ and $R^4$ is a glycoside moiety. The latter embodiment relates to compounds that are often found in vegetable sources along with compounds where all of $R^1$, $R^2$, $R^3$ and $R^4$ are hydrogen. In some interesting embodiments, all of $R^1$, $R^2$, $R^3$ and $R^4$ are selected hydrogen.

The term "glycoside moieties" is intended to mean a mono- or disaccharide moiety, e.g. derived from O-galactopyranose, O-glucopyranose, O-galactopyranosylgalactopyranose, O-glucopyranosylgalactopyranose, O-galactopyranosylglucopyranose and O-glucopyranosylglucopyranose.

Also, it is envisaged that the compound (anti-inflammatory agent) preferably has the formula II:

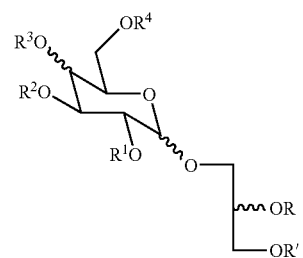

wherein R, R', $R^1$, $R^2$, $R^3$ and $R^4$ all are as defined above.

More specific examples of anti-inflammatory of particular interest are those selected from β-D-galactopyranosyl derivatives, α-D-galactopyranosyl derivatives, β-D-glucopyranosyl derivatives, and α-D-glucopyranosyl derivatives, such as β-D-galactopyranosyl and 6-O-(α-D-galactopyranosyl)-β-D-galactopyranosyl derivatives.

Even more specific examples of anti-inflammatory agents of interest are 3-β-D-galacto-pyranosyloxy-2-(octadeca-9Z, 12Z,15Z-trienoyloxy)propanyl octadeca-9Z,12Z, 15Z-trienoate, 3-β-D-glucopyranosyloxy-2-(octadeca-9Z,12Z, 15Z-trienoyloxy)propanyl octadeca-9Z, 12Z, 15Z-trienoate, 3-α-D-galactopyranosyloxy-2-(octadeca-9Z, 12Z,15Z-trienoyloxy)propanyl octadeca-9Z,12Z,15Z-trienoate, 3-α-D-glucopyranosyloxy-2-(octadeca-9Z,12Z,15Z-trienoyloxy)propanyl octadeca-9Z,12Z,15Z-trienoate, 6-O-(α-D-galactopyranosyl)-3-β-D-galactopyranosyloxy-2-(octadeca-9Z,12Z,15Z-trienoyloxy)-propanyl octadeca-9Z,12Z,15Z-trienoate and 6-O-(α-D-galactopyranosyl)-3-α-D-galactopyranosyloxy-2-(octadeca-9Z,12Z,15Z-trienoyloxy) propanyl octadeca-9Z,12Z,15Z-trienoate, such as 3-β-D-galactopyranosyloxy-2-(octadeca-9Z,12Z,15Z-trienoyloxy)-propanyl octadeca-9Z,12Z,15Z-trienoate or 3-β-D-glucopyranosyloxy-2-(octadeca-9Z,12Z,15Z-trienoyloxy)propanyl octadeca-9Z,12Z,15Z-trienoate, e.g. 3-β-D-galacto-pyranosyloxy-2-(octadeca-9Z,12Z,15Z-trienoyloxy)propanyl octadeca-9Z,12Z,15Z-trienoate which can be isolated from rose-hips.

As already mentioned above, the anti-inflammatory agent may be prepared by total or partial synthesis according to the methods known in the art (see, e.g., Nagatsu et al., Bioorg. and Medicinal Chem. Vol. 4, 1619–1622, 1994; Ohta et al., Chem. Pharm., Vol 39, 1337–1339, 1991; Shibuya et al. Chem. Pharm., Vol. 40, 1166–1169, 1992), or the anti-inflammatory agent may be isolated from rose-hips or other vegetative sources. Alternatively, the anti-inflammatory agent may be present in a plant extract or material, preferably a plant extract or material enriched or standardised with respect to the anti-inflammatory agent.

When isolated from rose-hips, the rose-hips are harvested in a generally known manner when the hips are fully ripe. Hips from wild rose bushes, such as *Rosa canina* ("dog rose-hip"), *Rosa gallica, Rosa condita, Rosa rugosa, Rosa hugonis, Rosa nitida, Rosa pendulina, Rosa pimpinellifolia,* and *Rosa sericea* may advantageously be used. The antiinflammatory agent is preferably obtained by extraction from dried and milled rose-hips through solvent extraction, using organic or inorganic solvents such as hexane, dichloromethane, ethanol, or water, though others may be used. After extraction, the obtained extract is evaporated to dryness, to recover an extract fraction containing the anti-inflammatory agent, or, depending on the extraction steps, the anti-inflammatory agent itself is obtained as an isolate, as will be discussed further below.

As an example, 3-β-D-galactopyranosyloxy-2-(octadeca-9Z,12Z,15Z-trienoyloxy)propanyl octadeca-9Z,12Z,15Z-trienoate (Formula III) was isolated from dried powder of dog-rose hip. The isolated compound not only potently inhibits oxidative burst response but do also inhibit chemotaxis of human leukocytes.

of a dynamic complex of cytological and chemical reactions that occur in the affected blood vessels and adjacent tissue in response to injury or abnormal stimulation caused by physical, chemical or biological agent, including the local reactions and resulting morphologic changes, the destruction of removal of the injurious material, and the responses that lead to repair and healing". Examples of relevant inflammatory conditions are hepatitis, meningitis, rheumatoid arthritis, inflammatory bowl diseases such as Crohn's disease, allergic syndromes, diabetes, congestive heart disease, psoriatic, reactive or osteo-arthritis or other arthritides such as osteoarthrosis, multiple sclerosis, atherosclerosis, sepsis/septic shock, dermal inflammation, graft rejection, and inflammation secondary to chemotherapy or radiotherapy of neoplastic disease.

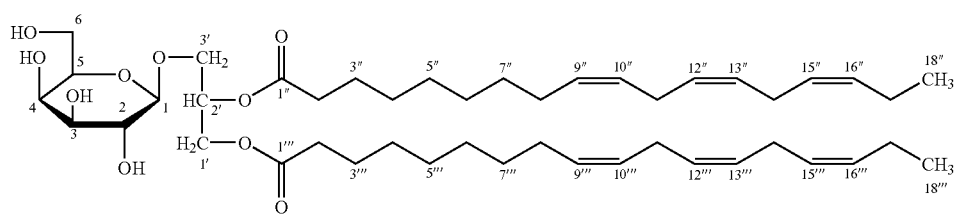

Formula III

GOPO

While an isolated compound may be used, an enriched or standardised plant extract or standardised plant material obtained in the process of complete isolation may also be useful in the present invention, particularly as the extracted or standardised product may be obtained at lower cost than the isolated compounds. In addition, other ingredients in the extract or plant material may support or enhance the effects of the anti-inflammatory agent, such as the vitamins (some of which may have an anti-oxidative effect) that remain after partial extraction. The choice of whether to treat inflammation with an enriched or standardised extract or standardised plant material as opposed to an isolated or synthesised product most likely will depend on the extent of the inflammatory disease. For example, with arthritis, those suffering minor discomfort would most likely be well served by administration of the enriched or standardised extract or standardised plant material, while those more seriously debilitated may seek to use the isolated or synthesised compound.

The inventors' observation that the compound of formula III compounds described herein inhibit the oxidative burst response as well as chemotaxis makes it reasonably to believe that it is an active contributor to the anti-inflammatory effect of the dried rose-hip powder. Thus, the inventors believe that this finding renders it probable that the anti-inflammatory agents described herein, either as isolated compounds or included in enriched or standardised extracts or enriched plant material, are suitable for the treatment of inflammatory conditions, e.g. those associated with arthritis.

A medicament (pharmaceutical composition) comprising the anti-inflammatory agent may be useful in the prevention, treatment or alleviation inflammation, whether caused by illness or medical conditions, such as viral or bacterial diseases (commonly termed "inflammatory conditions"). "Inflammation" is defined in Stedman's Medical Dictionary, 26$^{th}$ Edition as "a fundamental pathologic process consisting The present invention is presently believed to be particularly suitable for the treatment of arthritis and osteoarthrosis.

Formulation

As mentioned above, the anti-inflammatory agent may be used directly as the pure compounds or as a constituent of an enriched or standardised plant extract or a standardised dried plant material.

Thus, the medicament may be in the form of an extract of a plant material, typically an extract where the concentration of the anti-inflammatory agent is known to the extent that the dose given to the mammal can be controlled.

Regardless of form, but in particular when the compound is in the form of a pure compound, it is normally necessary to formulate the compound so as to ease the application thereof to the mammal in need therefor, an so as to ensure suitable bioavailability of the compound.

The anti-inflammatory agents are preferably formulated in a pharmaceutically acceptable carrier (or excipient), optionally in combination with an anti-oxidant. They may also be combined with other active ingredients to synergise the anti-inflammatory effects or to offer other supplemental benefits to the user.

Thus, the anti-inflammatory agent or an enriched or standardised extract or a standardised plant material containing the anti-inflammatory agent may be formulated alone or with other ingredients, as powders, granules, tablets, suspensions, solutions or emulsions and containing ingredients known in the art for preparing such formulation and be packaged in single or multiple daily dose forms.

In particular, a pharmaceutical composition (medicament) typically comprises from about 0.1 to about 50% by weight of the anti-inflammatory agent in a pharmaceutically acceptable carrier, preferably in combination with an anti-oxidant.

Administration may proceed by oral, buccal, parenteral, topical, rectal, transdermal or intranasal administration, though oral administration is preferred.

"Pharmaceutically acceptable carriers" as used herein are those media generally acceptable for use in connection with the administration of to mammals, including humans.

The term "mammal" is intended to include larger mammals such as humans as well as domestic or farm animals such as horses, dogs, sheep, pigs, cows, etc. Among these mammals, humans are particularly interesting subjects to benefit form the invention.

Pharmaceutical compositions are generally formulated according to a number of factors well within the purview of the ordinarily skilled artisan to determine and account for, including without limitation: the particular anti-inflammatory agent, its concentration, stability and intended bioavailability; the specific inflammatory disease, disorder or condition (collectively: "condition") being treated with the medicament; the subject, its age, size and general condition; and the composition's intended route of administration, e.g., oral, buccal, parenteral, topical, rectal, transdermal or internasal administration. Typical pharmaceutically acceptable carriers used in parenteral drug administration include, for example, DSW, an aqueous solution containing 5% weight by volume of dextrose, and physiological saline. Pharmaceutically acceptable carriers can contain additional ingredients, for example those that enhance the stability of the active ingredients included, such as preservatives and anti-oxidants.

In one embodiment, the medicament comprises an antioxidant in combination with the compound defined herein and the pharmaceutically acceptable carrier. The anti-oxidant is, e.g., an anti-oxidant selected from Vitamin C and derivatives thereof, Vitamin E, flavonoides, phenolic acids such as methyl, ethyl or n-propyl p-hydroxybenzoate, carotenes, butylated hydroxyanisoles, butylated hydroxytoluenes, nordihydroguaiaretic acid, etc. This embodiment is particularly relevant where the anti-inflammatory agent comprises one or more unsaturated bonds such as double bonds, which might make the compound susceptible to oxidative degradation.

The pharmaceutical composition may be administered parenterally by injection, infusion or implantation (intravenous, intramuscular, intraarticular, subcutaneous or the like) In dosage forms, formulations or e.g. suitable delivery devices or implants containing conventional, non-toxic pharmaceutically acceptable carriers and adjuvants.

The formulation and preparation of such compositions is well-known to those skilled in the art of pharmaceutical formulation. Specific formulations can be found in Remington: The Science and Practice of Pharmacy by Alfonso R. Gennaro (Editor), 20th edition (2000), Lippincott, Williams & Wilkins; ISBN: 0683306472.

The anti-inflammatory agent is typically formulated in a pharmaceutically acceptable aqueous medium.

Thus, the pharmaceutical compositions may comprise the anti-inflammatory agent in the form of a sterile injection. To prepare such a composition, the suitable anti-inflammatory agent is dispersed in a parenterally acceptable liquid vehicle which conveniently may comprise suspending, solubilising, stabilising, pH-adjusting agents and/or dispersing agents. Among acceptable vehicles that may be employed are water, water adjusted to a suitable pH by addition of an appropriate amount of hydrochloric acid, sodium hydroxide or a suitable buffer, 1,3-butanediol, Ringer's solution and isotonic sodium chloride solution.

The anti-inflammatory agent can be formulated for delivery via various routes of administration. Oral administration is preferred for ease of use. A unit dosage can comprise a therapeutically effective amount of the anti-inflammatory agent for a single daily administration (e.g. orally or by feeding tube in an enteral diet for example), or be formulated to provide multiple doses per day. A unit dosage will depend on many factors including age, condition, and disease state, but in any event, the entire daily dosage will be that which is physiologically acceptable to the individual and can be administered daily over a prolonged period of time.

While still under investigation, it is believed that a dosage of from 0.001–50 mg/kg body weight per day, such as 0.005–20 mg/kg body weight per day (mg/kg/day), of the anti-inflammatory agent, would be effective in the treatment of the inflammatory condition, in particular arthritis and osteoarthrosis, and relief of the symptoms associated therewith. A similar to lesser dose rate could be administered on a daily basis as a prophylactic. A preferred unit dose is from about 0.001 to about 50, such as 0.001–20, mg/kg/day. The total daily dose would be about 0.1 to about 5000 mg/day, such as 0.5–500 mg/day. For example, the unit dose may be administered by compounding into tablets or capsules, each containing from 0.01–500 mg of 3-β-D-galactopyranosyloxy-2-(octadeca-9Z,12Z,15Z-trienoyloxy)propanyl octadeca-9Z,12Z,15Z-trienoate, the user taking from one to four capsules per day.

Although the focus of the invention discussed above is for human therapy, it is also contemplated to use the anti-inflammatory agent in the treatment or prophylaxis of non-human mammals, including domestic and farm animals, having an inflammatory condition caused for example by arthritis. The skilled artisan would readily ascertain the mode and method of therapy based on the animal to be treated. For example, the composition can be incorporated into the animal's water source or feed, or it can be administered as other medicaments, in the form of a tablet, capsule, liquid, emulsion, or the like.

As it is often required for regulatory reasons to standardise plant extracts or materials used as natural medicine for humans, a further aspect of the present invention relates to a method for standardising a natural medicine product with respect to one compound of the formula I:

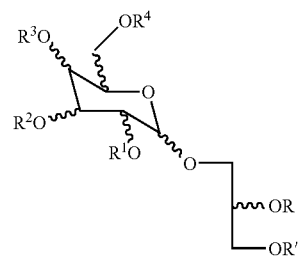

wherein R and R' independently are selected from hydrogen, $C_{10-24}$-alkyl, and $C_{10-24}$-acyl, said alkyl and acyl groups having 0 to 5 unsaturated bonds, and $R^1$, $R^2$, $R^3$ and $R^4$ independently are selected from hydrogen and glycoside moieties, with the proviso that not both of R and R' are hydrogen, as an active ingredient, said natural medicine product being intended for the treatment, alleviation or prophylaxis of inflammatory conditions in a mammal, the method comprising:
(a) providing a batch of a plant extract or material containing the compound of formula I;
(b) determining the concentration of the compound of formula I in said batch;
(c) preparing the natural medicine product in the form of unit dose forms each comprising a predetermined amount of the active ingredient, wherein the predetermined amount of the active ingredient is provided by a quantity of said batch, said quantity being determined as the predetermined amount of the active ingredient divided by the concentration of the active ingredient in said batch. The compound of formula I is preferably 3-β-D-galactopyranosyloxy-2-(octadeca-9Z,12Z,15Z-trienoyloxy)propanyl octadeca-9Z,12Z,15Z-trienoate. This aspect is further illustrated in Example 4.

While preferred embodiments of the present invention save been shown and described, it will be understood by those skilled in the art that various changes or modifications can be made without varying from the spirit and scope of the present invention, and the invention is not limited to the examples given.

human peripheral blood neutrophils in vitro. From these results, it was concluded that the activity in these assays was mainly if not exclusively confined to a single compound. This compound was purified by preparative HPLC and the structure identified by $^1$H—, $^{13}$C—, NOESY-, COSY-, and HETCOR-NMR experiments to be 3-β-D-galactopyranosyloxy-2-(octadeca-9Z,12Z,15Z-trienoyloxy)propanyl octadeca-9Z,12Z,15Z-trienoate (GOPO). The chemical structure was further confirmed by basic hydrolysis in methanol (methanolysis) and acidic hydrolysis. Basic hydrolysis afforded methyl linolenate as the only methyl ester as shown by GC-MS analysis, whereas acidic hydrolysis afforded D-galactose and glycerol as shown by analytical HPLC analysis.

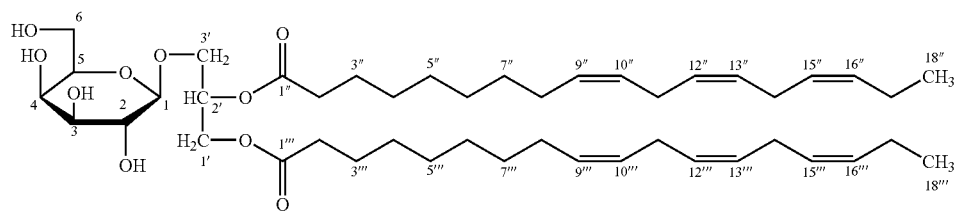

GOPO

Tables 1 and 2 shows the NMR data for the isolated active compound (GOPO). The NMR data (CD$_3$OD) of GOPO are fully in accordance with those found by Wegner et al. in Wegner, C., M. Hamburger, O. Kunert, and E. Haslinger. 2000. Tensioactive Compounds from the Aquatic Plant *Ranunculus fluitans* L. (Ranunculaceae). Helv. Chim. Acta 83:1454–1464 (Ref. 1).

EXAMPLE 1

This example illustrates how the active principle of rose-hip was isolated from extracts of rose-hips by activity guided fractionation and the methods used for the identification of the active compound (GOPO). This example also illustrates a method for the quantification of the active compound by analytical HPLC in for example hip-rose extracts.

Activity Guided Fractionation and Identification of the Active Compound

The active compound in the dog rose fruits was determined by activity guided fractionation. Thus, 1000 grams of dried and milled fruits were sequentially extracted with hexane, dichloromethane, methanol and water, and the extracts evaporated. The resulting residues were tested for inhibition of chemotaxis of human peripheral blood neutrophils in vitro. From these results it was determined that the active component(s) was present in the dichloromethane extract (FIG. 1). This extract was separated into clusters of components by silica gel chromatography using a gradient eluent of dichloromethane and methanol (starting with dichloromethane only and ending with methanol only) and the individual fractions tested for inhibition of chemotaxis of

TABLE 1

$^{13}$C-NMR spectral data (75 MHz, CDCl$_3$ or CD$_3$OD, δ-values in ppm) for GOPO.

| Assignments | Multiplicity* | $\delta_C$(CDCl$_3$) | $\delta_C$(CD$_3$OD) | $\delta_C$(CD$_3$OD) Data from Ref. 1 |
|---|---|---|---|---|
| C-1 | d | 104.3 | 106.3 | 105.4 |
| C-2 | d | 71.6 | 73.3 | 72.4 |
| C-3 | d | 73.7 | 75.7 | 74.9 |
| C-4 | d | 69.5 | 71.1 | 70.2 |
| C-5 | d | 74.8 | 77.7 | 76.8 |
| C-6 | t | 62.4 | 63.3 | 62.5 |
| C-1' | t | 63.1 | 64.9 | 64.0 |
| C-2' | d | 70.4 | 72.7 | 71.8 |
| C-3' | t | 68.4 | 69.6 | 68.7 |
| C-1", C-1''' | s | 174.1, 173.7 | 176.1, 175.8 | 175.0, 174.7 |
| C-2", C-2''' | t | 34.5, 34.3 | 36.0, 35.8 | 35.1, 35.0 |
| C-3", C-3''' | t | 25.1$^a$ | 26.8$^a$ | 26.6$^a$ |
| C-4", C-4''' | t | 29.8$^b$ | 31.6$^b$ | 30.8$^b$ |
| C-5", C-5''' | t | 29.5$^b$ | 31.2$^b$ | 30.4$^b$ |
| C-6", C-6''' | t | 29.4$^b$ | 31.1$^b$ | 30.3$^b$ |
| C-7", C-7''' | t | 29.3$^b$ | 31.0$^b$ | 30.2$^b$ |
| C-8", C-8''' | t | 27.4 | 29.0 | 28.2 |
| C-9", C-9''' | d | 132.2$^c$ | 133.8$^c$ | 132.7$^c$ |
| C-10", C-10''' | d | 130.4$^c$ | 132.1$^c$ | 131.1$^c$ |
| C-11", C-11''' | t | 25.9$^a$ | 27.4$^a$ | 26.4$^a$ |
| C-12", C-12''' | d | 128.6$^c$ | 130.2$^c$ | 129.2$^c$ |
| C-13", C-13''' | d | 128.5$^c$ | 130.2$^c$ | 129.2$^c$ |
| C-14", C-14''' | t | 25.8$^a$ | 27.3$^a$ | 26.0 |
| C-15", C-15''' | d | 128.0$^c$ | 129.9$^c$ | 128.9$^c$ |
| C-16", C-16''' | d | 127.3$^c$ | 129.2$^c$ | 128.3$^c$ |

TABLE 1-continued $^{13}$C-NMR spectral data (75 MHz, CDCl$_3$ or CD$_3$OD, δ-values in ppm) for GOPO.

| Assignments | Multiplicity* | δ$_C$(CDCl$_3$) | δ$_C$(CD$_3$OD) | δ$_C$(CD$_3$OD) Data from Ref. 1 |
|---|---|---|---|---|
| C-17″, C-17‴ | t | 20.8 | 22.3 | 21.5 |
| C-18″, C-18‴ | q | 14.5 | 15.5 | 14.7 |

*Multiplicity determined by DEPT and HETCOR-NMR experiments.
Abbreviations for multiplicity: s = singlet, d = doublet, t = triplet, q = quartet.
a,b,cIn the same column: These assignments may be interchanged.

TABLE 2

$^1$H-NMR spectral data (300 MHz, CD$_3$OD, δ-values in ppm) for GOPO.

| H | δ$_H$ (multiplicity, J in Hz), CD$_3$OD | δ$_H$ (multiplicity, J in Hz), CD$_3$OD (Ref. 1) |
|---|---|---|
| 1 | 4.23 (d, 6.6) | 4.23 (d, 7.3) |
| 2 | 3.51 (dd, 6.6, 9.7) | 3.52 (dd, 7.4, 9.8) |
| 3 | 3.45 (dd, 2.1, 9.7) | 3.45 (dd, 3.3, 10.3) |
| 4 | 3.84 (dd, 0.5, 2.1) | 3.83 (dd, 1.0, 2.5) |
| 5 | 3.48 (m) | 3.48 (m) |
| 6a | 3.73 (dd, 6.6, 12.0) | 3.71 (m) |
| 6b | 3.75 (dd, 4.4, 12.0) | 3.76 (m) |
| 1′a | 4.22 (dd, 6.9, 12.0) | 4.23 (dd, 7.3, 13.6) |
| 1′b | 4.43 (br d, 12.0) | 4.44 (dd, 3.0, 12.1) |
| 2′ | 5.27 (m) | 5.26 (m) |
| 3′a | 3.71 (dd, 5.4, 11.0) | 3.70 (dd, 5.4, 11.2) |
| 3′b | 3.98 (dd, 5.4, 10.8) | 3.97 (dd, 5.4, 10.9) |
| 2″, 2‴ | 2.32 (br t, 7.0) | 2.32 (m) |
| 3″, 3‴ | 1.60 (m) | 1.59 (m) |
| 4″–7″, 4‴–7‴ | 1.35 (m) | 1.32 (m) |
| 8″, 17″, 8‴, 17‴ | 2.08 (m) | 2.08 (m) |
| 9″, 10″, 12″, 13″, 15″, 16″ 9‴, 10‴, 12‴, 13‴, 15‴, 16‴ | 5.35 (m) | 5.33 (m) |
| 11″, 14″, 11‴, 14‴ | 2.82 (br t, 6.8) | 2.80 (m) |
| 18″, 18‴ | 0.98 (t, 7.5) | 0.97 (t, 7.5) |

Abbreviations for multiplicity: d = doublet, dd = double doublet, m = multiplet, t = triplet. br = broad.

Materials and Method

Dried and milled fruits of dog rose (*Rosa canina* L.) were obtained from Hyben Vital International ApS (Tullebølle, Denmark). HPLC-grade hexane, methanol (CH$_3$OH), acetonitrile (CH$_3$CN), dichloromethane (CH$_2$Cl$_2$), and tetrahydrofuran (THF) were obtained from Merck (Darmstadt, Germany). Silica gel 60 (0.063–0.200 mm) and analytical (0.1 mm) silica gel 60 F$_{254}$ plates (TLC plates) were also obtained from Merck. Analytical TLC plates were developed using 10% H$_2$SO$_4$ in CH$_3$OH followed by heating.

Extraction Procedure

Dog rose powder (1000 g) were submerged in hexane (2 L) for 24 hours, filtered and the powder washed with hexane (2×500 mL). The combined hexane solutions were evaporated to dryness under reduced pressure. The powder was then submerged in CH$_2$Cl$_2$ (2 L) for 24 hours, filtered and the residual powder washed with CH$_2$Cl$_2$ (2×500 mL). The combined CH$_2$Cl$_2$ solutions were evaporated to dryness under reduced pressure. The powder was then submerged in CH$_3$OH (2 L) for 24 hours, filtered and the powder washed with CH$_3$OH (2×500 mL). The combined CH$_3$OH solutions were evaporated to dryness under reduced pressure. Finally the powder was submerged in water (2 L) for 24 hours, filtered and the powder washed with water (2×500 mL). The combined water solutions were evaporated to dryness under reduced pressure (FIG. 1).

Chromatographic Conditions

The residue from evaporation of the CH$_2$Cl$_2$ solutions were dissolved in 100 mL CH$_2$Cl$_2$ and the solution placed on a silica gel column (500×40 mm i.d.) in hexane. The column was eluted with a stepwise gradient (1 L) of CH$_3$OH in CH$_2$Cl$_2$ (0, 1, 2, 5, 10, 20, and 100% CH$_3$OH). Each fraction (100 mL) was analyzed by analytical TLC and, if relevant, evaporated to dryness under reduced pressure.

Preparative HPLC Conditions

For preparative HPLC a Merck L-6200 intelligent pump and a Merck L-4200 UV-VIS detector were used. Separations were performed at 35° C. on a Develosil ODS-HG-5 (RP-18, particle size 5 μm; 250×20 mm i.d., Nomura Chemical Co., Japan) column protected with a guard cartridge (50×20 mm i.d.) packed with the same material as the column, using the following gradient: 150 mL 25% CH$_3$CN (aq); 150 mL 50% CH$_3$CN(aq); 150 mL 60% CH$_3$CN(aq); 150 mL 70% CH$_3$CN(aq); 150 mL 80% CH$_3$CN(aq); 150 mL 90% CH$_3$CN(aq) and 300 mL 100% CH$_3$CN. Compounds were detected at 203 nm. Flow rate: 5 mL min$^{-1}$. Injection volume: 5 mL.

Analytical HPLC Conditions

Figure 2:
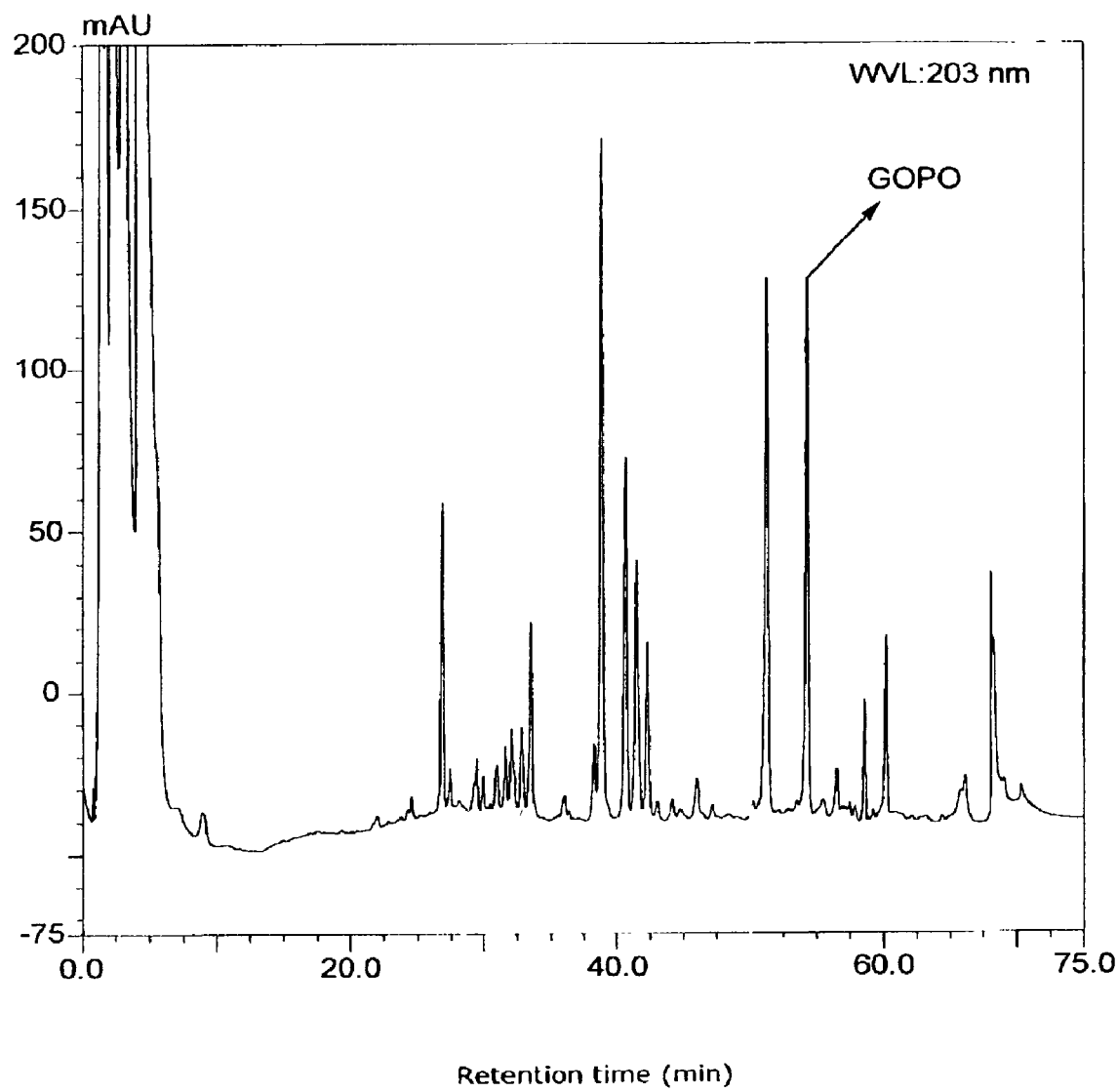
FIG. 2 shows a typical analytical HPLC chromatogram of a THF extract from dried and milled peels of dog rose fruits (*Rosa canina* L.) obtained from Hyben Vital International ApS. Furthermore the retention time of the active compound (GOPO) is indicated.

Analytical HPLC was performed on a SUMMIT/Dionex HPLC system equipped with a photodiode array detector (wavelength range 195–700 nm). The purity of the Isolated compounds were determined at 35° C. by reversed phase analytical HPLC on a LiChrospher 100 RP-18 (particle size 5 μm; 244×4 mm i.d., Merck) column using the following gradient: 0–10 min (100% solvent B); 10–25 min (100–50% solvent B, 0–50% solvent A); 25–55 min (50–0% solvent B, 50–100% solvent A); 55–64 min (100% solvent A); 64–74 min (100–80% solvent A, 0–20% solvent C); 74–85 min (80% solvent A, 20% solvent C); 85–95 min (80–100% solvent A, 20–0% solvent C); 95–105 min (100–0% solvent A, 0–100% solvent B); and 105–110 min (100% solvent B). All changes in the gradient are linear programmed. Solvent A: 100% CH$_3$CN. Solvent B.: 20% CH$_3$CN (aq). Solvent C: 100% THF. Compounds were detected at 203 nm. Data collection time: 0–75 min. Flow rate: 1 mL min$^{-1}$. Injection volume: 20 μL. Retention time for GOPO: approximately 54 min (FIG. 2).

From these tests, it was determined that an extraction process for obtaining the galactolipid composition comprises the steps of obtaining a plant material such as rose-hips, drying and milling the plant material (rose-hips) to form a powder, treating the powder with a first organic solvent, in which the galactolipid is insoluble, removing the organic solvent to form a first residue, which is the galactolipid containing fraction. The use of an initial organic solvent extraction step removes non-active constituents, to provide an increased concentration of the active extract fraction. The isolation of the galactolipid involves the steps of treating the first residue with an organo/chloro solvent to extract the galactolipid from the first residue, and removing the organo/chloro solvent to precipitate a galactolipid rich fraction.

It is also possible to obtain the galactolipid anti-inflammatory extract fraction by direct extraction of the rose-hip powder using the organo/chloro solvent, and removing the organo/chloro solvent to precipitate a galactolipid rich fraction.

EXAMPLE 2

This example illustrates the activity of the active component of Example 1 in different cell function assays.

Biological Data of GOPO 20 mg/ml of GOPO prepared in dimethylsulfoxide (DMSO) was obtained from the process described above and diluted in minimal essential medium (MEM), to final concentrations of 100 µg/ml, 50 µg/ml, 10 µg/ml, 1 µg/ml and 0.1 µg/ml for use in the cell function assays.

Polymorphonuclear Leukocytes

Polymorphonuclear leukocytes (PMNS) were isolated from the peripheral blood of healthy individuals in citrated glass. The cells were separated by dextran density gradient and lymphoprep separation. The purity of PMNs was greater than 98% and the cell viability as determined by trypan blue dye exclusion was greater than 98%.

Chemotaxis

Chemotaxis assay was performed using a modified Boyden chamber technique as described in Jensen, P. and Kharazmi, A., Computer-assisted image analysis assay of human neutrophil chemotaxis in vitro. J. Immunol. Methods, 144, 43–48. 1991. The purified PMNs were pre-incubated with different dilutions of the extracted galactolipid for 30 min at 37° C. Following preincubation, the chemotaxis of the cells towards the chemotactic factor zymosan activated serum (ZAS), which contains the biologically active chemoattractant C5a, were tested. The migrated cells were counted by a computer-assisted image analysis system.

Chemiluminescence

Chemiluminescence assay was used as a measure of oxygen radical generation by activated PMNs. The method was performed as described in Kharazmi, A., Høiby, N., Doring, G., and Valerius, N. H. Pseudomonas aeruginosa exoproteases inhibit human neutrophil chemiluminescence. Infect. Immun. 44, 587, 1984. PMNs were pre-incubated with different concentrations of the extracted galactolipid and then stimulated with opsonized zymosan. The oxidative burst response of the activated cells was measured by a luminometer (1250-LKB Wallace).

Results

Chemotaxis

Table 3 shows the results of the activity of GOPO, (100 µg/ml and 50 µg/ml dilutions) on chemotaxis of human peripheral blood polymorphonuclear leukocytes. The results are shown as the number of cells migrated and the percent inhibition.

TABLE 3

| Preparation | Cells migrated | Percent inhibition |
|---|---|---|
| GOPO (100 µg/ml) | 8 | 86 |
| GOPO (50 µg/ml) | 5 | 92 |
| DMSO control | 59 | 0 |

The same experiments as shown in Table 3 were repeated on a new batch of the active compound (GOPO). Table 4 shows the results of the activity of GOPO, (100 µg/ml, 10 µg/ml, 1 µg/ml and 0.1 µg/ml dilutions) on chemotaxis of human peripheral blood polymorphonuclear leukocytes. The results are shown as the number of cells migrated and the percent inhibition.

TABLE 4

| Preparation | Cells migrated | Percent inhibition |
|---|---|---|
| GOPO (100 µg/ml) | 12 | 71 |
| GOPO (10 µg/ml) | 16 | 62 |
| GOPO (1 µg/ml) | 15 | 64 |
| GOPO (0.1 µg/ml) | 39 | 7 |
| DMSO control | 42 | 0 |

Table 5. Shows the results of chemiluminescence of human peripheral blood polymorphonuclear leukocytes. The results are shown as millivolts.

TABLE 5

| Preparation | Millivolts |
|---|---|
| GOPO (100 µg/ml) | 339 |
| GOPO (50 µg/ml) | 520 |
| DMSO control | 664 |

Table 6. Shows the results of cell viability. Cell viability was determined by a trypan blue dye exclusion method. The cells were incubated with trypan blue. The dead cells will take up dye and appear blue under the microscope. The results are show as percent viable cells.

TABLE 6

| Preparation | Percent viability |
|---|---|
| GOPO (100 µg/ml) | 99 |
| GOPO (50 µg/ml) | 100 |
| DMSO control | 100 |

CONCLUSIONS

As shown in Tables 3 and 4, the isolated compound (GOPO) at fairly low concentrations inhibited the migration of human peripheral blood leukocytes towards the biologically active chemoattractant zymosan-activated serum, which contains C5a.

As shown in Table 5, the isolated compound at fairly low concentrations inhibited the chemiluminescence of human peripheral blood leukocytes. Chemiluminescence is a measure of oxidative burst response. This indicates that the isolated compound exhibits anti-oxidant activity. As the actual tissue damage caused by inflammatory cells such as PMN's and monocytes/macrophages, through the release of proteolytic and hydrolytic enzymes as well as toxic reactive oxygen radicals activated in the tissue and joints, the isolated compound should be a potent inhibitor of the oxidative burst response of the human peripheral blood polymorphonuclear leukocytes, the most important and abundant inflammatory cells.

As shown in Table 6, the cells were viable at concentrations of the compound, which inhibited chemotaxis and chemiluminescence, indicating that the inhibition of cell migration and oxidative burst is not related to toxicity. In other words the active compound does not appear to be toxic at the tested concentrations.

EXAMPLE 3

This example illustrates the concentration (mg/kg) of the active component of Example 1 and 2 In commercial hip-rose products.

Analysis of commercial products of dog rose for GOPO by analytical HPLC.

The analytical HPLC method described under the section 'Analytical HPLC conditions' was validated with regard to specificity, repeatability, intermediate precision, accuracy, linearity, range and robustness according to the ICH-guidelines from the European Commission (Volume 3 A Guidelines; Medicinal products for human use; Quality and biotechnology 1998 Edition) and was used to quantify GOPO in commercially available products of dog rose. In Table 7 the results from the analysis of 10 commercial dog rose products for GOPO is shown.

TABLE 7

| Commercial products | GOPO (mg/kg dog rose product) |
|---|---|
| Hyben Vital | 303.0 |
| CP 1 | 75.8 |
| CP 2 | 72.7 |
| CP 3 | 62.1 |
| CP 4 | 51.5 |
| CP 5 | 40.9 |
| CP 6 | 18.2 |
| CP 7 | 15.2 |
| CP 8 | 6.1 |
| CP 9 | 6.1 |

CP = anonymous commercial product.

EXAMPLE 4

Use of the invention to prepare a standardised preparation.

According to the guidelines issued by the Danish Medicines Agency (Laegemiddelstyrelsen), a natural medicine must be standardised, to contain a specified amount of a compound that is specific for the plant or animal substance that it is prepared from. If a compound exists that is recognised as being responsible for the clinical effect of the drug, it is defined as the active compound and must be used for the standardisation. If no active compound is known, the producer can choose another characteristic compound as a marker compound for standardisation. Since the present invention indicates that GOPO is the active compound in rose hip preparations that can alleviate pains due to arthritis, it must be used for standardisation of any rose hip preparation that is registered as a natural medicine. Similar regulations for the registration of standardised preparations of herbal products etc. exist in other countries.

If a product is standardised according to a compound such as GOPO, this means that each unit, e.g. tablet or capsule, contains enough plant material to provide a defined amount of GOPO. If for example the unit dose is defined as 0.1 mg, and the concentration in the product is measured as 303 mg/kg, as described in Example 3, Table 7, each unit made from this batch of material must contain 0.330 g of the crude product.

For practical reasons, rather than adjusting the amount of material used in each tablet or capsule, the crude product is diluted by as much as is needed in order to obtain the desired concentration, and then a fixed amount of the diluted product is used for each tablet or capsule. For example, to make capsules with a content of 500 mg material and a unit dose of 0.1 mg GOPO from a batch of plant material containing 303 mg/kg, it must be diluted to a concentration of 200 mg/kg. This can be accomplished by adding to the crude product an amount of chalk powder or other inert material corresponding to 51.1% of the weight of the crude product. Then each capsule containing 500 mg diluted material will also contain 0.1 mg GOPO, and thereby meet the requirements for a standardised product.

Alternatively, a high quality batch, e.g. one containing 303 mg/kg as above, can be mixed with a batch of lower quality, e.g. one containing 75.8 mg/kg.

In this case the mixture would contain 54.6% of the high quality batch, providing 165.6 mg GOPO/kg, and 45.4% of the low quality batch, providing 34.4 mg/kg, in order to obtain in total the desired standardised concentration of 200 mg/kg.

In any case, when the active compound is used for standardisation, the standard concentration must be chosen so the final product contains a lower concentration of active compound than the best part of the raw materials. The general principle outlined here is applicable to any of the types of compounds described in the text, and present in any source material.

The invention claimed is:

1. A method of treating or alleviating at least one inflammatory condition causing chemotaxis of mammal leucocytes in a mammal in need therefore, said inflammatory condition is arthritis or an inflammatory bowel disease, said method comprising the step of administering a dosage of from 0.005–20 mg/kg body weight per day of a medicament comprising an isolated compound of the formula I:

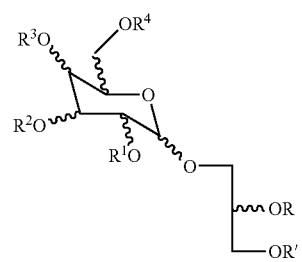

wherein R and R' independently are selected from hydrogen, $C_{10-24}$-alkyl, and $C_{10-24}$-acyl, said alkyl and acyl groups having 0 to 5 unsaturated bonds, and $R^1$, $R^2$, $R^3$ and $R^4$ independently are selected from hydrogen and glycoside moieties, wherein the glycoside moieties are either mono- or disaccharide moieties; with the first proviso that not both of R and R' are hydrogen, and with the second proviso that none of R and R' is eicosapentaenoyl, to the body of said mammal, wherein said mammal is selected from the group consisting of humans as well as domestic or farm animals.

2. The method according to claim 1, wherein R and R' independently are selected from $C_{10-24}$-alkyl and $C_{10-24}$-acyl groups, said alkyl and acyl groups having 0 to 5 unsaturated carbon-carbon bonds.

3. The method according to claim 1, wherein any alkyl and acyl groups have 0 to 4 unsaturated carbon-carbon bonds.

4. The method according to claim 1, wherein any unsaturated carbon-carbon bonds are double bonds.

5. The method according to claim 2, wherein R and R' both are $C_{16-20}$-acyl having 1 to 3 double bonds.

6. The method according to claim 1, wherein the compound has the formula II:

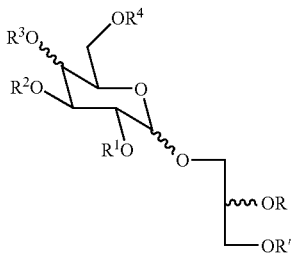

wherein R, R', $R^1$, $R^2$, $R^3$ and $R^4$ all are as defined in claim 1.

7. A method of treating or alleviating at least one inflammatory condition causing chemotaxis of mammal leucocytes in a mammal in need therefore, said method comprising the step of administering a dosage of from 0.005–20 mg/kg body weight per day of a medicament comprising an isolated compound of the formula I:

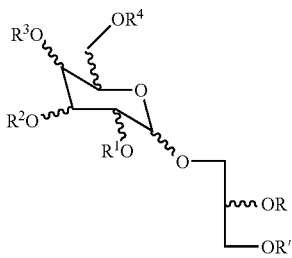

wherein R and R' independently are selected from hydrogen, $C_{10-24}$-alkyl, and $C_{10-24}$-acyl, said alkyl and acyl groups having 0 to 5 unsaturated bonds, and $R^1$, $R^2$, $R^3$ and $R^4$ independently are selected from hydrogen and glycoside moieties, wherein the glycoside moieties are either mono- or disaccharide moieties; with the first proviso that not both of R and R' are hydrogen, and with the second proviso that none of R and R' is eicosapentaenoyl, to the body of said mammal, wherein said mammal is selected from the group consisting of humans as well as domestic or farm animals, wherein the compound is selected from the group consisting of: 3-β-D-galactopyranosyloxy-2-(octadeca-9Z, 12Z, 15Z-trienoyloxy)propanyl octadeca-9Z, 12Z, 15Z-trienoate, 3-β-D-glucopyranosyloxy-2-(octadeca-9Z, 12Z, 15Z-trienoyloxy)propanyl octadeca-9Z, 12Z, 15Z-trienoate, 3-α-D-galactopyranosyloxy-2-(octadeca-9Z, 12Z, 15Z-trienoyloxy)propanyl octadeca-9Z, 12Z, 15Z-trienoate, and 3-α-D-glucopyranosyloxy-2-(octadeca-9Z, 12Z, 15Z-trienoyloxy)propanyl octadeca-9Z, 12Z, 15Z-trienoate.

8. The method according to claim 1, wherein the inflammatory condition is selected from the group consisting of: rheumatoid arthritis, and reactive or osteo-arthritis.

9. The method according to claim 1, wherein the inflammatory condition is arthritis.

10. The method according to claim 1, wherein the inflammatory condition is osteoarthrosis.

11. The method according to claim 1, wherein the medicament comprises one or more compounds of the formula I in a total concentration of 0.1–50% by wt. based on the total weight of the medicament.

12. The method according to claim 1, wherein the medicament further comprises an anti-oxidant.

13. The method according to claim 1, wherein the medicament is provided to the mammal by oral, buccal, parenteral, rectal, transdermal or internasal administration.

14. The method according to claim 1, wherein the compound is at least partially synthesized or isolated from rose hips.

15. The method according to claim 1, wherein the compound is a diacylglycerol.

16. The method according to claim 15, wherein the compound is a monogalactosyl diacylglycerol.

17. A standardised product, based on rose hip material comprising rose hip material and a predetermined amount in a unit dose form in the range of 0.01 to 500 mg of an active ingredient defined by the compound of the formula I:

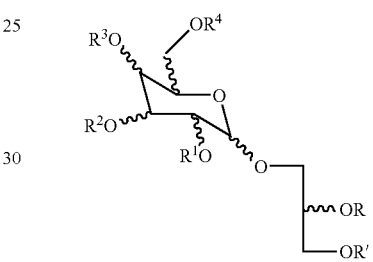

wherein R and R' independently are selected from hydrogen, $C_{10-24}$-alkyl, and $C_{10-24}$-acyl, said alkyl and acyl groups having 0 to 5 unsaturated bonds, and $R^1$, $R^2$, $R^3$ and $R^4$ independently are selected from hydrogen and glycoside moieties, wherein the glycoside moieties are either mono- or disaccharide moieties with the proviso that not both of R and R' are hydrogen.

18. The product according to claim 17, wherein the active ingredient is 3-α-D-galactopyranosyloxy-2-(octadeca-9Z, 12Z, 15Z-trienoyloxy)propanyl octadeca-9Z, 12Z, 15Z-trienoate.

19. A product according to claim 17, wherein the product is prepared in the form of unit dose forms each comprising a predetermined amount of the active ingredient, wherein the predetermined amount of the active ingredient is provided by a quantity of said batch, said quantity being determined as the predetermined amount of the active ingredient divided by the concentration of the active ingredient in said batch.

20. A product according to claim 17, wherein the active ingredient is provided in a predetermined unit dose forms in the range of 0.001–50 mg/kg body weight.

21. The method according to claim 1, wherein the mammal is selected from the group consisting of horses, dogs, sheep, pigs, and cows.

* * * * *

UNITED STATES PATENT AND TRADEMARK OFFICE
CERTIFICATE OF CORRECTION

PATENT NO.      : 7,084,122 B2
APPLICATION NO. : 10/300831
DATED           : August 1, 2006
INVENTOR(S)     : Erik Larsen et al.

It is certified that error appears in the above-identified patent and that said Letters Patent is hereby corrected as shown below:

- Column 7, line 26: "DSW" should be replaced by --D5W--
- Claim 18, line 44: "α" should be replace by --ß--

Signed and Sealed this

Twenty-sixth Day of December, 2006

JON W. DUDAS
*Director of the United States Patent and Trademark Office*